United States Patent [19]
Bourgeois-Jacquet et al.

[11] Patent Number: 5,971,619
[45] Date of Patent: Oct. 26, 1999

[54] SINGLE ROW BEARING RING WITH MONITORING DEVICE

[75] Inventors: Pierre Bourgeois-Jacquet, Avallon, France; Godfrey Hands, Nuneaton, United Kingdom

[73] Assignee: SKF Industrial Trading & Development Company B.V., Nieuwegein, Netherlands

[21] Appl. No.: 09/009,384

[22] Filed: Jan. 20, 1998

[30] Foreign Application Priority Data

Jan. 24, 1997 [NL] Netherlands .............................. 1005088

[51] Int. Cl.$^6$ ..................................................... F16C 19/06
[52] U.S. Cl. ............................................................. 384/448
[58] Field of Search ..................... 384/448, 446, 384/624, 490, 517

[56] References Cited

U.S. PATENT DOCUMENTS 4,798,299  1/1989  Bayer et al. ............................. 384/448
5,074,677  12/1991  Andree et al. ........................... 384/448

FOREIGN PATENT DOCUMENTS

A-001 474   4/1979   European Pat. Off. .
A-175 441   3/1984   European Pat. Off. .
B-228 731   7/1987   European Pat. Off. .
A-3-941 267 6/1990   Germany .

Primary Examiner—Lenard A. Footland
Attorney, Agent, or Firm—Oliff & Berridge, PLC

[57] ABSTRACT

A bearing comprises two opposing ring and a single row of rolling balls accommodated in the raceways of each of the rings. At least one of the rings carries an ultrasonic scanning device for scanning specific areas of the other ring upon relative rotation of the rings. The ultrasonic scanning device is opposite the other ring next to the raceway of said ring, and is directed such that ultrasonic waves produced thereby impinge upon the raceway of the other ring sidewardly.

16 Claims, 1 Drawing Sheet

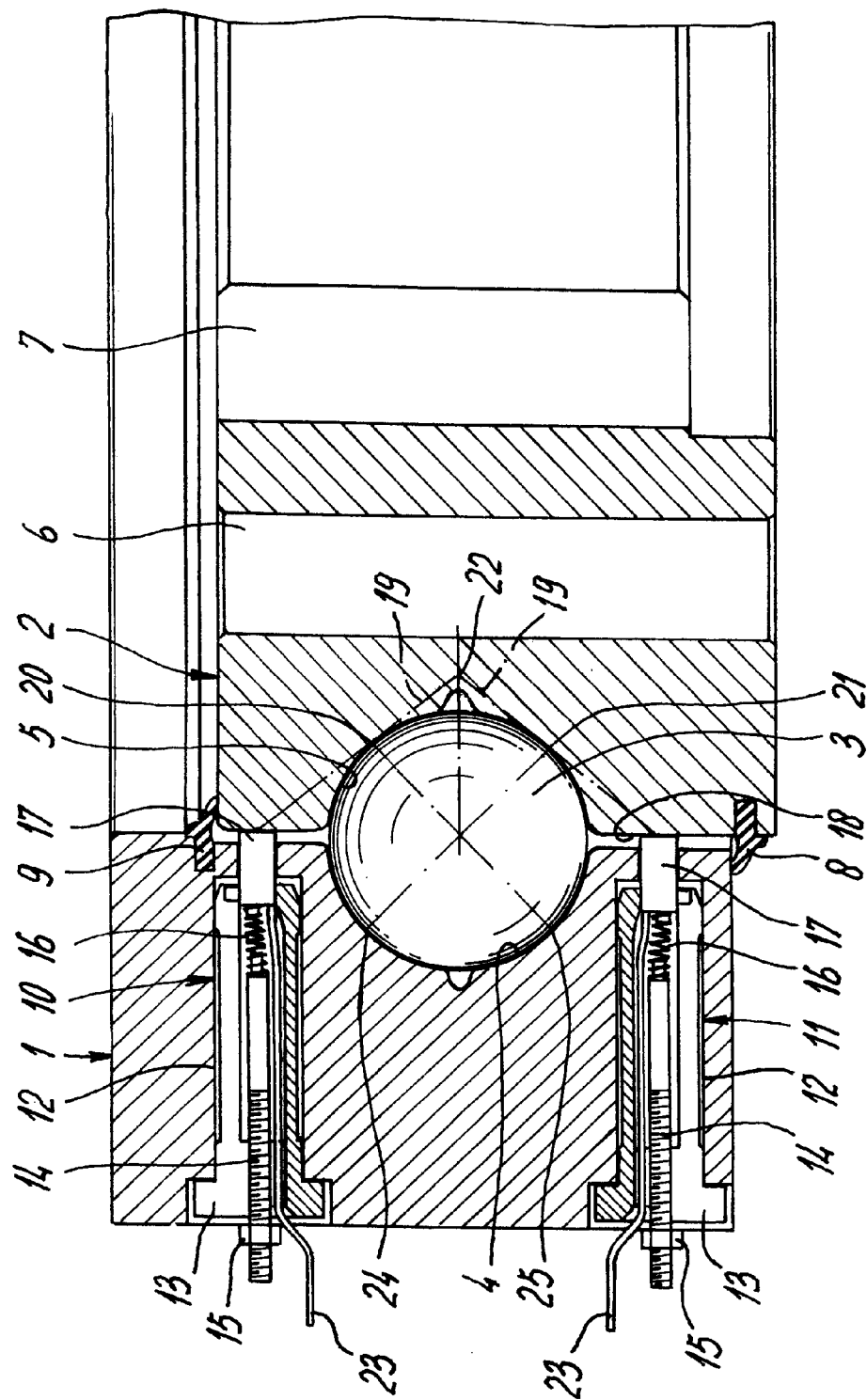

SINGLE ROW BEARING RING WITH MONITORING DEVICE

The invention is related to a bearing comprising two opposing rings, and a single row of rolling balls accommodated in the raceways of each of the rings. In particular, the invention is related to large size bearings, for example a slewing bearing. Such slewing bearings are usually applied in a harsh environment, such as in offshore cranes or earth moving equipment. They carry a very heavy, slow moving axial load which is unbalanced.

In particular, the severe conditions to which cranes on North Sea oil and gas platforms are subjected, pose a high risk. In order to avoid catastrophic failures of the bearings, authorities have stipulated that they are to be regularly inspected. This involves the removal of the crane so as to make the bearing accessible for inspection. This procedure is very time consuming, and results in an almost unacceptable downtime of the crane. Moreover, the costs involved in such inspection are high.

The slewing bearings are to be inspected in particular with respect to crack development in critical areas. Small cracks are usually accepted, in particular in case crack propagation is rather slow due to the materials and metallurgical processes employed in the manufacturing process. However, regular checking is necessary to ensure that the slewing bearing is replaced as soon as the cracks become too large The object of the invention is provide a method enabling the detection of surface and subsurface damage of the raceways and cracks in slewing bearings having a single row of rolling balls, without having to dismantle the crane for that purpose. This object is achieved in that at least one of the rings carries an ultrasonic scanning device for scanning specific areas of the other ring upon relative rotation of the rings.

This bearing according to the invention has the advantage of permitting uninterrupted inspection over 360° of the ring being inspected.

By means of the ultrasonic scanning device, the rings can be inspected without dismantling the crane. Thereby, the downtime of the crane is greatly reduced. Moreover, the scanning results obtained are highly reliable due to the fact that both the surface area of the raceways, as well as the internal structure of the ring in question can be examined.

In particular, the ultrasonic scanning device can be opposite the other ring next to the raceway of said ring, and can be directed such that ultrasonic waves produced thereby impinge upon the raceway of the other ring at an angle. By this impinging action of the ultrasonic waves, a high resolution is obtained which further enhances the scanning ability of the sensors.

Preferably, the ultrasonic waves impinge upon the raceway at an angle lying between 35 and 70 degrees with respect to a radial line; in particular, the ultrasonic waves may impinge upon the raceway at an angle lying between 35 and 55 degrees. Very good results are obtained in case the ultrasonic waves impinge upon the raceway at an angle of about 45 degrees.

In order to obtain a reliable scan of the complete cross section of the ring in question, one of the rings may carry two ultrasonic scanning devices which are situated on opposite sides of the raceway of the other ring. These ultrasonic scanning devices are directed such that their ultrasonic waves impinge upon opposite parts of the raceway of the other ring sidewardly. In this embodiment, the highly loaded areas of in particular a four-point contact ball bearing are fully covered by the sensors.

Preferably, the ultrasonic scanning devices are directed such that their ultrasonic waves intersect each other at an area lying beyond the raceway.

Reference is made to the slewing ring monitoring device as known from EP-B-228731. This device comprises ultrasonic sensors for the detection of cracks in specific areas, such as the nose and raceways, of a ring comprising three separate series of rollers. With this known device, it is not possible to inspect specific areas of a ring having only one series of balls, such as a four-point contact ball bearing.

Subsequently, the invention will be described further with reference to an embodiment shown in the FIGURE.

The FIGURE shows a four-point contact ball slewing bearing having an outer ring 1, and inner ring 2 and a series of balls supporting these rings 1 and 2 mutually. The balls 3 are contained in the raceway 4 of the outer ring and in the raceway 5 of the inner ring.

In service, the outer ring 1 is connected to a supporting structure, such as the pedestal of a crane. Onto the inner ring 2, the crane structure itself is mounted. To that end, holes 6 are provided in the inner ring which may accommodate mounting bolts. Also, the inner ring on its inner circumference is provided with a tooth rack 7, which can cooperate with a pinion for rotating the crane structure.

As is common practice, seals 8, 9 have been provided in order to seal the bearing space between the rings 1, 2.

According to the invention, two sensor devices 10, 11 have been inserted in radial holes 12 in the outer ring. The sensor devices 10, 11 comprise a housing 13, a shaft 14, as well as a means 15 for fixing the shaft 14 in a certain position within housing 13. The other end of the shaft 14 is supplied with a means for pressing the ultrasonic sensors against the outer circumference 18 of the inner ring 2 or inner circumference of the outer ring.

The sensors have been directed in such a way, that the path of the ultrasonic waves emitted thereby is oblique, as indicated by lines 19. These paths of the ultrasonic waves impinge upon the raceway 5 of the inner ring 2. In particular, they impinge upon the points 20, 21, which are the most highly loaded areas of a four-point ball bearing.

By means of the sensors 17, it is therefore possible to obtain a very accurate assessment of the area of the raceway 5, and of the underlying structure of the inner ring 2 which is subjected to the highest stresses.

The paths 19 of the ultrasonic waves intersect each other at a spot 22 lying beyond the raceway 5. Thereby, also this rather highly loaded area can be scanned accurately.

Although the FIGURE shows two sensor devices 10, 11 which are able to scan the inner ring. It is of course also possible to insert sensor devices in the inner ring for scanning of corresponding areas in the outer ring.

Although in the description, reference is made to an embodiment shown, the outer ring of which is connected to a supporting structure, an alternative embodiment with the inner ring connected to the supporting structure is also possible. In that case, the tooth rack will be located on the outer circumference of the outer ring. It is also possible that the tooth rack can be located on the non-rotating ring.

We claim:

1. A bearing comprising two opposing rings and a single row of rolling balls accommodated in raceways of each of the rings, wherein at least one of the rings carries an ultrasonic scanning device opposite the other ring for scanning specific areas of the other ring upon relative rotation of the rings, the ultrasonic scanning device being directed such that ultrasonic waves produced thereby impinge upon the raceway of the other ring sidewardly at an angle lying between 35 and 70 degrees with respect to a radial line of the bearing.

2. A bearing according to claim 1, wherein the bearing is a four-point contact ball bearing.

3. A bearing according to claim 1, wherein the ultrasonic scanning device comprises a sensor which is preloaded against the other ring.

4. A bearing according to claim 1, wherein the ultrasonic waves are at an angle lying between 35 and 55 degrees.

5. A bearing according to claim 1, wherein the ultrasonic waves are at an angle of about 45 degrees.

6. A bearing according to claim 1, wherein one of the rings carries two ultrasonic scanning devices which are situated on opposite sides of the raceway of the other ring.

7. A bearing according to claim 6, wherein the ultrasonic scanning devices are directed such that their ultrasonic waves impinge upon opposite parts of the raceway of the other ring.

8. A bearing according to claim 7, wherein the ultrasonic scanning devices are directed such that their ultrasonic waves intersect each other at an area lying beyond the raceway.

9. A bearing according to claim 1, wherein the ultrasonic scanning device is accommodated in a through going hole of the bearing ring.

10. A bearing according to claim 9, wherein each hole is about radially oriented.

11. A bearing comprising two opposing rings and a single row of rolling balls accommodated in raceways of each of the rings, wherein at least one of the rings carries an ultrasonic scanning device for scanning specific areas of the other ring upon relative rotation of the rings, wherein the ultrasonic scanning device is accommodated in a through going hole of the bearing ring, the through going hole being about radially oriented.

12. A bearing according to claim 11, wherein one of the rings carries two ultrasonic scanning devices which are situated on opposite sides of the raceway of the other ring.

13. A bearing according to claim 11, wherein the bearing is a four-point contact ball bearing.

14. A bearing comprising two opposing rings and a single row of rolling balls accommodated in raceways of each of the rings, wherein at least one of the rings carries an ultrasonic scanning device for scanning specific areas of the other ring upon relative rotation of the rings, wherein the ultrasonic scanning device comprises a sensor which is preloaded against the other ring.

15. A bearing according to claim 14, wherein the bearing is a four-point contact ball bearing.

16. A bearing according to claim 14, wherein one of the rings carries two ultrasonic scanning devices which are situated on opposite sides of the raceway of the other ring.

* * * * *